United States Patent [19]

Utz et al.

[11] Patent Number: 5,500,219

[45] Date of Patent: Mar. 19, 1996

[54] PESTICIDE COMPOSITIONS CONTAINING BLENDS OF BLOCK COPOLYMERS WITH ANIONIC SURFACTANTS HAVING IMPROVED DISSOLUTION RATES

[75] Inventors: Christopher G. Utz, Wyandotte, Mich.; Rebecca P. Hollis, Flemington, N.J.; Johnny M. Sekmistrz, Wyandotte, Mich.

[73] Assignee: BASF Corporation, Mount Olive, N.J.

[21] Appl. No.: 124,413

[22] Filed: Sep. 21, 1993

[51] Int. Cl.$^6$ .......................... A01N 25/14; A01N 25/12
[52] U.S. Cl. .......................................... 424/409
[58] Field of Search ................... 424/405, 401, 424/409, 400

[56] References Cited

U.S. PATENT DOCUMENTS

| | | | |
|---|---|---|---|
| 4,826,618 | 5/1989 | Borseth et al. | 252/174.21 |
| 5,049,303 | 9/1991 | Secenski et al. | 252/548 |
| 5,169,894 | 12/1992 | Holland et al. | 524/502 |

FOREIGN PATENT DOCUMENTS

| | | |
|---|---|---|
| 0225287 | 6/1987 | European Pat. Off. . |
| 1542875 | 6/1970 | Germany . |

*Primary Examiner*—Peter F. Kulkosky
*Attorney, Agent, or Firm*—Nixon & Vanderhye

[57] ABSTRACT

A surfactant/polymer blend with a dissolution rate in water of not greater than 6.5 minutes has 85 to 95% EO/PO block copolymers having in excess of 70% EO, 5 to 15% of one or more polycarboxylates, and 0.1 to 5% of at least one linear alkylbenzene sulfonate.

13 Claims, No Drawings

PESTICIDE COMPOSITIONS CONTAINING BLENDS OF BLOCK COPOLYMERS WITH ANIONIC SURFACTANTS HAVING IMPROVED DISSOLUTION RATES

FIELD OF THE INVENTION

The present invention relates to surfactant blends of ethylene oxide/propylene oxide (EO/PO) block copolymers and anionic polymers and surfactants. These blends have increased dissolution rates when compared with the EO/PO blocks by themselves, and are useful as dispersants in agricultural applications, particularly in pesticide formulations.

BACKGROUND OF THE INVENTION

Block copolymers of ethylene oxide and propylene oxide are well known nonionic surfactants. Their unique hydrophilic/hydrophobic character translates into a broad range of surfactant functions and physical properties. Their exceptional versatility has led to their widespread use in diverse markets and applications. Many of these surfactants are valued for their defoaming/antifoaming, cleaning, solubilization, foaming, emulsification and wetting properties, among others.

EO/PO block copolymer surfactants also function extremely well as dispersants in aqueous media, particularly in pesticide formulations. A dispersion is a system containing solid particles in a liquid continuous phase. A pesticidal dispersion will therefore contain particles of active material spread throughout the liquid medium. A good surfactant or dispersant will therefore inhibit the natural tendency of the solid particles to stick together, or recombine. Flocculation and hard agglomeration are thus two problems which dispersants are designed to help prevent.

The dissolution rates of the EO/PO block copolymers will to a large extent determine their suitability as dispersants of active solids. The better the dissolution rate, the better the ability of the surfactant to stabilize the solid in the liquid system. Unfortunately for many EO/PO block copolymers, their dissolution rates can be sufficiently slow so as to preclude their use as dispersants in many instances.

One particularly efficacious group of nonionic surfactant dispersants is represented by the formula:

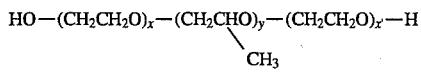

where x, y and x' are numbers such that the block copolymer is greater than 50% hydrophilic and often more than 70% hydrophilic, and the molecular weight ($M_w$) of the hydrophobe is between 950 and 4000. These compounds have total molecular weights in excess of 1000 and are marketed under the trademark PLURONIC® by BASF Corporation. Of special note is the EO/PO block copolymer represented by the above formula and having a total molecular weight of about 8,400. This compound is available under the trademark PLURONIC® F68.

While the above compounds have been used for many years as dispersants, notably as additives in pesticide formulations, there has been a need to improve the dissolution rates of these compounds without sacrificing their performance characteristics such as suspensibility and settling. Currently, the dissolution rates for the compounds described above are in excess of 11 minutes. While this has been satisfactory for end users of pesticide formulations, it is not ideal.

Anionic surfactants have been combined with nonionic surfactants such as EO/PO block copolymers. Holland et al., U.S. Pat. No. 5,169,894 relates to dispersants for inorganic pigment slurries with polycarboxylates and nonionic EO/PO copolymer surfactants. In this context, the nonionic surfactant is utilized to lower anionic loading on the pigment, and the polyacrylate is the major component of the blend in amounts of as much as 90%. Holland et al. fail to discuss how to increase the dissolution rate of the nonionic surfactant through addition of the anionic component thereto.

Thus there presently exists a need in the art for one or more dispersants made from EO/PO block copolymer surfactant blends having considerably faster dissolution rates and excellent performance features.

OBJECTS OF THE INVENTION

It is therefore an object of the present invention to formulate dispersants for aqueous media having improved dissolution rates.

Another object of the invention is to provide blends of nonionic ethylene oxide/propylene oxide block copolymers with anionic polymers and surfactants for use as dispersants with faster dissolution rates.

A further object of the invention is to have improved dispersants for agricultural applications, notably pesticide formulations.

Also an object of the present invention is to increase the dissolution rates of EO/PO copolymer surfactant dispersants without substantially affecting their performance specifications.

SUMMARY OF THE INVENTION

These and other objects of the invention are achieved by providing a surfactant/polymer blend with a dissolution rate in water of not greater than about 6.5 minutes. The blend contains about 85 to about 95% EO/PO block copolymers having more than about 50% EO, about 5 to about 15% of one or more polycarboxylates, and about 0.1 to about 5% of at least one linear alkylbenzene sulfonate (LAS). The surfactant blends of the invention find excellent utility in agricultural applications, specifically as dispersants for pesticide formulations. In this regard, a pesticide formulation is also provided which contains the improved surfactant/polymer blend(s) herein described.

Also provided as part of the invention is a method of increasing the dissolution rate of an ethylene oxide/propylene oxide block copolymer which comprises adding thereto an effective amount of at least one compound selected from the group consisting of polycarboxylates and linear alkylbenzene sulfonates. In many instances, the dissolution rate of the EO/PO block copolymer can be increased by as much as about 50% or more.

DETAILED DESCRIPTION OF THE PREFERRED EMBODIMENTS

The surfactant blend according to the various embodiments of the invention has at least one nonionic ethylene oxide/ propylene oxide (EO/PO) block copolymer surfactant component with the following formula:

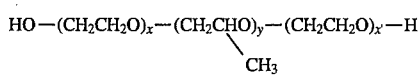

where x, y and x' are numbers such that ethylene oxide (EO) comprises greater than about 50%, more preferably greater than about 70% of the total molecular weight ($M_w$), and wherein the $M_w$ of the propylene oxide (PO) hydrophobe is between about 950 and about 4000 (unless otherwise stated, all molecular weights herein are expressed as weight average molecular weight or $M_w$). It is desirable that these compounds have total molecular weights within the range of about 6000 to about 15,000, or even more preferably within the range of about 9000 to about 15,000. Especially desirable EO/PO block copolymers are part of the PLURONIC® series available from BASF Corporation. Especially preferred is the EO/PO block copolymer represented by the above formula and having a total molecular weight of about 8400. This compound is available as PLURONIC® F68. Also useful as EO/PO block copolymers as part of the invention are PLURONIC® F128 with a molecular weight of about 12,600, and PLURONIC® F108 with a molecular weight of about 14,600.

The nonionic surfactant component will comprise between about 85 and about 95% by weight of the polymer blend (unless otherwise stated, all percentages are expressed as weight percents based upon the total weight of the blend or composition). In a more preferred embodiment, the EO/PO block copolymer will make up between about 88 and about 92%. It is even more desirable that the nonionic copolymer surfactant comprise about 89 to about 90% by weight of the total surfactant blend.

Also part of the dispersant blend of the invention are one or more anionic polymers. The anionic polymer component of the blend will comprise one or more polycarboxylates. Preferably, these polycarboxylates are polyacrylates. Those polyacrylates having a molecular weight of less than or equal to about 12,000 are especially preferred. More preferred are the polyacrylates with molecular weights within the range of about 1200 to about 8000. It is especially desirable that one of the anionic components of the blend composition according to the invention be a polyacrylate having a molecular weight of about 4000. This compound is available under the trademark SOKOLAN® PA-30 from BASF Corporation.

The above anionic polycarboxylate component(s) of the dispersant blend will be present in an amount of from about 5 to about 15% of the blend composition. Preferably, this component will comprise about 8 to about 12% of the composition. In an especially desirable embodiment, the anionic component heretofore set forth will make up about 10% of the blend composition. The weight percentages herein expressed for the polycarboxylate component are based upon percentage of active material, since these polycarboxylates are typically dissolved in water.

Also part of the dispersant blend according to the invention are one or more anionic compounds selected from the group consisting of the linear alkylbenzene sulfonates. It has now been discovered that the addition of relatively small amounts of at least one linear alkylbenzene sulfonate to the blend of nonionic surfactant and anionic polycarboxylate heretofore described markedly improves the dissolution rate (hereinafter described) of the blend. The alkylbenzene sulfonate component(s) is preferably selected from the group of $C_8$ to $C_{20}$ linear alkylbenzene sulfonates. More preferred are those compounds wherein the alkyl group is a member of $C_8$ through $C_{15}$ alkyl. Especially desirable are $C_{12}$ through $C_{15}$ linear alkylbenzene sulfonates, including mixtures thereof.

The linear alkylbenzene sulfonate component of the blend composition will comprise from about 0.1 to about 5% of the total blend. It is more preferred that this component be present in amounts of from about 0.1 to about 2.5% of the composition. More efficacious will be those blends which contain linear alkylbenzene sulfonate in amounts of from about 0.5 to about 1.5%. In one especially preferred embodiment, the linear alkylbenzene sulfonate will make up about 1% of the total blend composition.

To prepare the surfactant/polymer blend formulation according to the various embodiments of the invention, those skilled in the art may wish to first melt the EO/PO block copolymer surfactant component since these compounds are usually present as solids or pastes. Next, this component is thoroughly mixed with the polycarboxylate and linear alkylbenzene sulfonate components by stirring, the latter two components being in liquid form. After mixing is complete, the blend is exposed to a cold surface, for example, a freezer-stored stainless steel bowl, to harden the melt. The blend may then be granulated or flaked for further use or study.

The surfactant/polymer blend according to the invention will have a dissolution rate of less than about 6 and ½ minutes in water. More preferably, the dissolution rate will be less than about 6 minutes. It is also within the scope of the invention that the claimed surfactant/polymer blend will dissolve in water at a rate of less than about 5 and ½ minutes. The term "dissolution rate" as used herein is based on the following protocol:

Add 190 g of 342 ppm water Ca/Mg hardness to a 400 mL beaker. Stir the water slowly with a magnetic stirrer causing no vortex. Add 10 grams of 14–20 mesh sieve fraction of surfactant/polymer blend and start a stopwatch. Dissolution is complete when no solid surfactant material can be discerned with the naked eye. At that point the watch is stopped and the total time measured.

The following example, and all examples herein, is presented to illustrate one or more aspects of the invention and should not be construed as limiting the scope thereof:

EXAMPLE 1

Example 1 (as set forth in TABLE 1) illustrates the dissolution rates in minutes for various preferred embodiments of the invention, as well as sets forth comparative examples:

TABLE 1

DISSOLUTION TIMES FOR SURFACTANT/POLYMER BLENDS

| SURFACTANT | DISSOLUTION TIME (MIN) |
|---|---|
| 1. PLURONIC F68 | 11:15 |
| 2. 95:5 F68/SOKALAN PA-30 | 10:42 |
| 3. 90:10 F68/PA-30 | 7:24 |
| 4. 94:5:1 F68/PA-30/LAS | 5:56 |
| 5. 89:10:1 F68/PA-30/LAS | 5:29 |
| 6. 88:10:2 F68/PA-30/LAS | 6:05 |

*LAS - mixture of $C_{12}$–$C_{15}$ linear alkylbenzene sulfonates.

Those skilled in the art will note that the dissolution rate of 1.) the EO/PO block copolymer nonionic surfactant alone is in excess of 11 minutes. Addition of polycarboxylate to the block copolymer in 2.) and 3.) improves the dissolution rate. It should thus be evident to the skilled artisan that addition of polycarboxylate alone to the EO/PO block copolymer nonionic surfactant is within the scope of the invention.

Upon addition of the linear alkylbenzene sulfonate to the blends in 4.), 5.) and 6.) the dissolution rates markedly improve. The dissolution rates of blends 4.), 5.) and 6.) are all under 6 and ½ minutes.

The surfactant/polymer blend according to the invention will find ready application as a dispersant for active solids, particularly pesticides in pesticide formulations. The pesticide may be any known to those skilled in the art, and can include, for example, the compound atrazine (2-chloro-4-ethylamino-6-isopropylamino-s-triazine). It is expected that the term "pesticide" will also encompass other related agents such as, but not limited to, fungicides, herbicides and biocides.

The pesticide will typically comprise from about 70 to about 99.9% of the pesticidal formulation, more preferably from about 80 to about 92%.

The pesticide formulation will further comprise the surfactant/polymer blend according to its various embodiments heretofore set forth in amounts of from about 0.1 to about 15% of the pesticide composition, preferably in amounts of from about 1 to about 10% thereof. It is especially preferred that the pesticide composition have about 2 to about 8% of the surfactant/polymer blend.

The pesticide formulation may also contain wetting agents, as well as other compounds known in the art. Water may comprise the remainder of the pesticide formulation, although the pesticide composition will usually be marketed without water. The agricultural customer will typically add water in measured amounts for application to crops, etc. in the fields.

EXAMPLE 2

Example 2 illustrates that the performance factors of various pesticide granulations containing the dispersant surfactant/polymer blends of the invention are minimally affected or in some instances actually improve, as compared with the same formulations having only the EO/PO block copolymer surfactant as the dispersant. The following granulations were made:

| 90% Atrazine | or | 92% Atrazine |
| --- | --- | --- |
| 3% BASOWET ® BX wetting agent | | 2% BASOWET ® BX wetting agent |
| 7% Surfactant | | 3% Surfactant |
| | | 2% BENTONITE ® HMP-20 clay filler |
| | | 1% Residual water |

The procedure for making the above granulations was as follows:

The batches were mixed in a V-blender and milled through a 0.022 inch screen. The milled material was granulated on a 16 inch pan at an angle of 60° C. Granules were sieved and the fraction between 12 and 40 mesh was tested.

Each granule type was tested for particle size through a wet sieve analysis, hardness, suspensibility, wetting time, settling and redispersibility. TABLE 2 sets forth the results:

TABLE 2

SURFACTANT PERFORMANCE IN WATER DISPERSIBLE GRANULES

| SURFACTANT | % FORMULA | ON 50 MESH (%) | ON 325 MESH (%) | % SUSPENSI- BILITY | SETTLING 30 MIN (ML) | HARDNESS (% BKDOWN) | WETTING TIME (SEC) |
| --- | --- | --- | --- | --- | --- | --- | --- |
| PLURONIC F68 | 3 | 4.84 | 1.56 | 51.50 | 2.00 | 95.40 | 8 |
| F68/SOKALAN PA30/LAS | 3 89/10/1 | 5.08 | 2.32 | 67.50 | 2.10 | 81.36 | 8 |
| F68/PA30/LAS | 3 88/10/2 | 8.88 | 2.40 | 68.50 | 2.70 | 74.00 | 8 |
| PLURONIC F68 | 7 | 6.72 | 3.08 | 70.50 | 1.60 | 51.32 | 15 |
| F68/PA30/LAS | 7 88/10/2 | 3.92 | 2.12 | 71.50 | 1.30 | 71.12 | 10 |

It is expected that the surfactant/polymer blends of the invention with increased dissolution rates may also find utility as dispersants in other applications wherein ethylene oxide/propylene oxide block copolymers are utilized, and the dissolution rate thereof is to be increased.

While the invention has been described in each of its various embodiments, it is expected that certain modifications thereto may be made by those skilled in the art without departing from the true spirit and scope of the invention as set forth in the specification and the accompanying claims.

What is claimed is:

1. A granular agricultural pesticide composition, comprising:
   a) from about 70 to about 99.9% of a pesticide; and
   b) from about 0.1 to about 15 percent of at least one dispersant surfactant/polymer blend with a dissolution rate in water of not greater than about 6.5 minutes, said blend consisting essentially of:
      1) about 85 to about 95% EO/PO block copolymers having at least about 70% EO;
      2) about 5 to about 15% of one or more polycarboxylates; and
      3) about 0.1 to about, 5% of at least one linear alkylbenzenesulfonate.

2. A composition as claimed in claim 1, comprising about 0.5 to about 5% of said at least one linear alkylbenzenesulfonate.

3. A composition as claimed in claim 2, wherein said EO/PO block copolymer has a molecular weight of greater than or equal to about 6000.

4. A composition as claimed in claim 3, wherein said polycarboxylates are polyacrylates having a molecular weight within the range of about 1200 to about 12,000.

5. A composition as claimed in claim 4, wherein said linear alkylbenzenesulfonate has a $C_8$ to $C_{18}$ alkyl group.

6. A composition as claimed in claim 5, wherein said EO/PO block copolymer is present in an amount of from about 88 to about 92%.

7. A composition as claimed in claim 6, wherein said polyacrylate is present in an amount of from about 8 to about 12%.

8. A composition as claimed in claim 7, wherein said linear alkylbenzenesulfonate is present in an amount of from about 0.1 to about 2.5%.

9. A composition as claimed in claim 8, wherein said blend has a dissolution rate of not greater than about 6 minutes.

10. A composition as claimed in claim 9, wherein said EO/PO block copolymer has a molecular weight of about 8400 and is present in an amount of from about 89 to about 90%.

11. A composition as claimed in claim 10, wherein said polyacrylate has a molecular weight of about 4000 and is present in an amount of about 10%.

12. A composition as claimed in claim 11, wherein said linear alkylbenzenesulfonate has a $C_{12}$ to $C_{15}$ group and is present in an amount of from about 0.5 to about 1.5%.

13. A composition as claimed in claim 12, wherein said surfactant blend has a dissolution rate of not greater than about 5.5 minutes.

* * * * *